United States Patent [19]

Sabesan

[11] Patent Number: 5,128,463
[45] Date of Patent: Jul. 7, 1992

[54] PROCESS FOR THE PREPARATION OF 2-DEOXY SUGARS

[75] Inventor: Subramaniam Sabesan, Wilmington, Del.

[73] Assignee: E. I. Du Pont de Nemours and Company, Wilmington, Del.

[21] Appl. No.: 645,518

[22] Filed: Jan. 24, 1991

[51] Int. Cl.$^5$ ............... C08B 31/08; C07H 15/04; C07H 15/207; A61K 35/14
[52] U.S. Cl. ............... 536/124; 536/116; 536/18.6; 536/114; 536/111
[58] Field of Search ............ 536/18.6, 18.4, 115, 536/124, 122; 514/34; 568/697

[56] References Cited

U.S. PATENT DOCUMENTS

| | | | |
|---|---|---|---|
| 4,362,720 | 12/1982 | Lemieux et al. | 536/116 |
| 4,739,043 | 4/1988 | Defaye et al. | 536/18.6 |
| 4,831,128 | 5/1989 | Tsai et al. | 536/124 |

OTHER PUBLICATIONS

Corry, E. J. et al., J. Am. Chem. Soc. 1980, vol. 102, 1439–1441.
Hadfield, A. F. et al., Carbohydr. Res. 1982, vol. 101; 197–208.
Ciment, D. M. et al., J. Chem. Soc. (c) 1966.
Monneret, C., et al., Carbohydr. Res. 191, vol. 96, 299–305.
Giese, B. et al., Liebigs Ann. Chem. 1988, 615–617.
Bolitt et al., J. Org. Chem. vol. 55, 5812-13, (1990).
Buttersack, C. et al., Reactive Polymers, vol. 5, 171–180, 1987.
Takiura, K. et al., Carbohydr. Chem. 1972, vol. 23, 369–377.
Takiura, K. et al., Carbohydr. Res. 1972, vol. 21, 379–391.
Maki, T. et al., Chem. Pharm. Bull (Tokyo) 1967, vol. 15, 1069.

*Primary Examiner*—Ronald W. Griffin
*Assistant Examiner*—L. Leary

[57] ABSTRACT

A one-step reaction process is provided for the preparation of 2-deoxy-hexopyranoses and 2-deoxy-hexopyranosides. Also provided is a process for specially activating sulfonic acid resin for catalysis of the above one-step preparation of 2-deoxy sugars.

9 Claims, No Drawings

PROCESS FOR THE PREPARATION OF 2-DEOXY SUGARS

FIELD OF THE INVENTION

This invention relates to a process for the preparation of 2-deoxy hexopyranoses and 2-deoxyhexopyranosides.

BACKGROUND OF THE INVENTION

2-Deoxy hexopyranoses are present in numerous biologically active natural compounds including compactin, olivimycin, mithramycin and daunomycin. The chemical synthesis of these natural products requires the ready availability of various 2-deoxy sugars in large quantities (Corey, E. J.; Weigel, L. O.; Chamberlin, A. R.; Lipshutz, B. J. Am. Chem. Soc. 1980, 102, 1439-1441). A number of reports have appeared describing methods for the preparation of 2-deoxy sugars. Most of these methods require at least two separate steps for the preparation of the desired 2-deoxy sugar. For example, 2-deoxy pyranoses and pyranosides have been obtained from glycals by hydration or hydroalkoxylation, catalyzed by methanolic hydrogen halide (Hadfield, A. F.; Sartorelli, A. C. Carbohydr. Res. 1982, 101, 197-208) or methanesulfonic acid (Ciment, D. M.; Ferrier, R. J. J. Chem. Soc. (C) 1966); by alkoxymercuration followed by borohydride reduction (Takiura, K.; Honda, S. Carbohydr. Chem. 1972, 23, 369-377; (Takiura, K.; Honda, S. Carbohydr. Res. 1972, 21, 379-391); by treatment with hydrogen halides in acetic acid (Maki, T.; Tejima, S. Chem. Pharm. Bull. (Tokyo) 1967, 15, 1069); by halohydration or alkoxylation followed by dehalogenation (Monneret, C.; Choay, P. Carbohydr. Res. 1981, 96, 299-305); and by trialkyltin hydride reduction of acylglycopyranosyl halides (Giese, B.; Gilges, S.; Gröninger, K. S. Lamberty, C.; Witzel, T. Liebigs Ann. Chem. 1988, 615-617).

The most direct method for the synthesis of 2-deoxy hexopyranoses or pyranosides would be via the acid catalyzed addition of water or alcohol to acetylated glycals. Yet, this general methodology to prepare 2-deoxy sugars has remained unworkable because the protected glycals often give rearranged products under acidic condition. To date, only one preparation based on this method has been reported: V. Bolitt et al., J. Org. Chem., 55, 5812-13, (1990). In this report Bolitt et al. describe the preparation of 2-deoxyglucopyranosides by the triphenylphosphine hydrobromide catalysed addition of alcohols to a single type of sugar, glucal compounds. This method is disadvantageous because its reported scope is limited solely to glucal compounds. Further, the catalyst, triphenylphosphine hydrobromide, is a neurologic hazard, an irritant and requires separation from crude reaction mixtures. Also, the method may not be suitable for the preparation of 2-deoxypyranoses, as water incompatible reaction solvent is used.

A more useful method for the preparation of 2-deoxyhexopyranoses would require only one step, would use commercially available non-toxic reagents and catalyst, would operate on a wide variety of sugar substrates and would provide pure product directly or with minimal purification effort. None of the above described methods possess all of the attributes of the ideal method. The object of the present method is to provide a one-step method for the preparation of 2-deoxyhexopyranoses and 2-deoxyhexopyranosides which possesses the above listed attributes.

SUMMARY OF THE INVENTION

This invention comprises a one-step reaction process for the preparation of 2-deoxyhexopyranoses and 2-deoxyhexopyranosides comprising the addition of water, alcohols or thiols to readily available glycals in the presence of a specially activated sulfonic acid resin and halide ions.

In practising the process of the present invention, a compound of Formula I is combined with a compound of Formula II, in the presence of a specially activated sulfonic acid resin and halide ions, to produce a compound of Formula III;

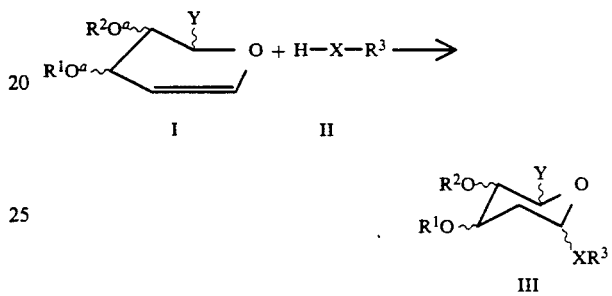

wherein:
$O^a$ and $O$ are each independently oxygen;
$R^1$ and $R^2$ are independently alkyl, alkenyl, alkynyl, aralkyl, aryl, acyl, aroyl, or a protected sugar, provided that for Formula I, the carbon of $R^1$ or $R^2$ directly bonded to $O^a$ is saturated; and for Formula II, the carbon of $R^3$ bonded to X is saturated;
Y is $(CH-OR^1)_nZ$, wherein:
Z is H or $CH_3$;
n is 0 to 4;
$R^1$ is defined as above;
X is oxygen or sulfur; and
$R^3$ is a hydrocarbyl, substituted hydrocarbyl, heterocyclic group, substituted heterocyclic group, or a protected sugar.

This invention further comprises a process for specially activating sulfonic acid resins comprising:

a) washing a commercial or noncommmercial sulfonic acid resin thoroughly with water;

b) treating the resin to remove water, which is accomplished by repeatedly washing the sulfonic acid resin with a water-miscible polar, aprotic solvent such as anhydrous reagent grade acetonitrile, dimethylforamide, acetone, or tetrahydrofuran; such washing is repeated 10 to 15 times in a volume of solvent at least equal to that of the resin; and c) drying the resin at room temperature for at least 3 hours under vacuum to remove residual solvent.

This invention further comprises specially activated sulfonic acid resins prepared by the above-described process, which are uniquely effective in the catalysis of reactions such as, for example, the one-step synthesis of 2-deoxy sugars from the corresponding glycals.

DETAILED DESCRIPTION OF THE INVENTION

The present invention provides a one-step reaction process for the preparation of 2-deoxy sugars, their α-glycosides and thio-glycosides, by the addition of water, alcohols or thiols to protected glycals. This process is accomplished by combining, in appropriate solvent, a compound of Formula I with a compound of Formula II, and stirring these reactants in the presence of a specially activated sulfonic acid resin and halide ions, to produce a compound of Formula III. The Formula III compound is then isolated and purified by techniques standard in the art.

The general reaction scheme is shown as follows:

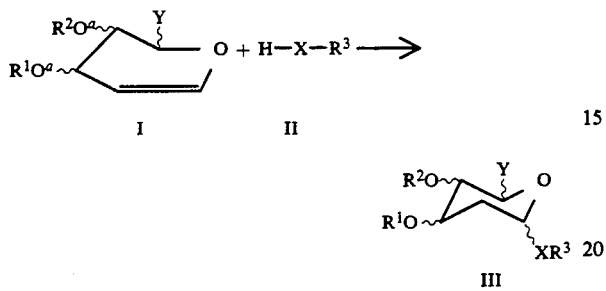

wherein:

$O^a$ and $O$ are each independently oxygen;

$R^1$ and $R^2$ are independently alkyl, alkenyl, alkynyl, aralkyl, aryl, acyl, aroyl, or a protective sugar, provided that for Formula I, the carbon of $R^1$ or $R^2$ directly bonded to $O^a$ is saturated (in other words, the carbon atom of the $R^1$ or $R^2$ moiety which is attached directly to the $O^a$ atom of Formula I must be a saturated carbon atom); and that for Formula II, the carbon of $R^3$ bonded directly to X is saturated;

Y is $(CH\text{-}OR^1)_nZ$, wherein:

Z is H or $CH_3$;

n is 0 to 4; and $R^1$ is defined as above;

X is oxygen or sulfur; and $R^3$ is a hydrocarbyl, substituted hydrocarbyl, heterocyclic group, substituted heterocyclic group, or a protective sugar.

The alkyl groups designated for $R^1$, $R^2$ or $R^3$ may be linear or branched chain, containing from 1 to 20 carbon atoms.

The alkenyl or alkynyl groups of $R^1$, $R^2$ or $R^3$ contain from one to twenty carbon atoms and may be linear or branched chain; provided that an unsaturated carbon of $R^1$, $R^2$ or $R^3$ may not be adjacent to the $O^a$ atom of Formula I, or the X of Formula II.

Aralkyl refers alkyl groups substituted with at least one aryl group.

Aryl refers to phenyl or naphthyl substituted with 0 to 3 of the following groups: alkyl, halogen, ether, oxo, ester, carboxy, amine, amide, sulfide, sulfoxide, sulfone, aryl, heterocyclic or substituted heterocyclic.

The acyl group may contain from 2 to 20 carbon atoms.

The aroyl group contains an aryl as defined above.

Protected sugar refers to a protected monosaccharide, disaccharide or polysaccharide.

Protected generally refers to when the hydroxy groups of the sugar moiety are functionalized so that they are not affected by the reaction conditions.

Hydrocarbyl refers to any alkyl, cycloalkyl, alkenyl, or aryl group.

Substituted hydrocarbyl refers to a hydrocarbyl group containing at least one of the following groups: halogen, ether, oxo, ester, carboxy, amine, amide, sulfide, sulfoxide, sulfone, aryl, heterocyclic or substituted heterocyclic.

The heterocyclic group may be any 5 or 6 membered mono- or polycyclic aromatic compound containing at least one oxygen, nitrogen or sulfur atom. Examples include, but are not limited to, furan, pyrrole, thiophene, pyridine, quinoline and isoquinoline.

A substituted heterocyclic group is a heterocycle as defined above containing at least one of the following groups: alkyl, cycloalkyl, alkenyl, aralkyl, aryl, halogen, ether, oxo, ester, carboxy, amine, amide, sulfide, sulfoxide or sulfone.

In the above reaction scheme, many aprotic solvents capable of solubilizing the halide ion source would serve as a suitable reaction solvent; such as, for example, acetonitrile, tetrahydrofuran, acetone, chloroform or nitromethane. The preferred reaction solvent is acetonitrile. The solvents dimethylforamide and dimethylsulfoxide are not useful.

The halide ions are provided in the form of soluble alkali metal chloride, alkali metal bromide or tetraalkylammonium chloride or bromide. Preferred are sodium bromide, lithium bromide, potassium bromide, n-tetrabutylammonium bromide or chloride, or tetraethylammonium bromide or chloride. Most preferred is lithium bromide.

Preferred compounds of Formula I are 3,4,6-tri-O-acetyl-D-glucal; 3,4,6-tri-O-acetyl-D-galactal; 3,4-di-O-acetyl-L-fucal; 3,4-di-O-acetyl-L-rhamnal; and D-lactal hexaacetate. Using any of these compounds, the addition of water or alcohol to glycals proceeds rapidly to give 2-deoxy hexopyranoses or hexopyranosides in high yield.

It is anticipated that an alcohol of any formula or a thiol of any formula will serve as a suitable Formula II compound in this reaction. Preferred compounds of Formula II are water, methanol, ethanol, propanol, butanol, allyl alcohol, 4-penten-1-ol, 5-methoxycarbonylpentan-1-ol and 1,2,3,4-di-O-isopropylidene-D-galactopyranose.

A "sulfonic acid resin" refers to the class of resins which are composed of sulfonic acid functional groups attached to a styrene divinylbenzene copolymer lattice. Commercial or non-commercial sulfonic acid resin may be used. A preferred sulfonic acid resin is the commercially available AG ® 50W-X2 (50–200 mesh) (Bio-rad, Richmond, Calif.).

The term "specially activated sulfonic acid resin" refers to a sulfonic acid resin which has been activated by thorough treatment with an organic solvent capable of effectively removing water from the resin. Any water-miscible polar, aprotic solvent, such as acetonitrile, acetone, tetrahydrofuran or dimethylformide will effectively specially activate such resins. Anhydrous reagent grade acetonitrile is the preferred activating solvent.

This invention further comprises a process for activating a sulfonic acid resin, as well as the resulting activated resin. In the activating process, the sulfonic acid resin is first washed thoroughly with water several times, especially if the resin has been newly obtained from a commercial source. Washing is performed until the wash filtrate is colorless; at a minimum, the resin is washed at least three times in a volume of water equal to the resin volume. The resin is then treated 10 to 15 times with an activating solvent, such as acetonitrile. The volume of activating solvent used in each individual washing is at least equal to the initial volume of the resin. These repeated washings are performed at room temperature and pressure. Typically during the washing procedure, the resin is immersed in the organic solvent, followed by gentle mixing with a spatula for one to two minutes. The resin is then drained with the use of water aspiration, until no more solvent drips from the funnel.

After such treatment, the activating solvent is then removed from the resin by thoroughly desiccating the resin for at least three hours, at room temperature, under vacuum. This activating treatment causes the resin to shrink considerably from its initial hydrous volume. After such processing, the activated resin is useful in the catalysis of reactions such as, for example, the one-step synthesis of 2-deoxy sugars from their corresponding glycals.

In practicing the process for preparation of 2-deoxy sugars of the present invention a solution containing a compound of Formula I, a compound of Formula II, and halide ion is stirred over a sulfonic acid resin activated as described above to produce a compound of Formula III. The compound of Formula III is then isolated and purified by techniques standard in the art.

The activated sulfonic resin is not capable of catalyzing the reaction by itself, addition of a source of halide ion is also required. Chloride and bromide effectively catalyze the reaction, and these halides may be added to the reaction mixture in the form of lithium bromide, sodium bromide, potassium bromide, tetraethylammonium chloride, tetraethylammonium bromide, n-tetrabutylammonium chloride or n-tetrabutylammonium bromide. Lithium bromide is the preferred source of halide ion.

The reaction process may be carried out at a temperature between 0° and 60° centigrade, preferably between 15° and 30°, and most preferably at room temperature. The process is complete within from 5 minutes to 24 hours of its commencement; the usual time range is between 5 minutes and 4 hours. The process is preferably carried out under an inert atmosphere such as nitrogen or argon. The process is carried out in conventional glassware, at atmospheric pressure. Molar ratio of Formula I compound to Formula II compound ranges from 1 to 2, to 1 to 20; with a catalytic amount of halide ions and specially activated sulfonic acid resin necessarily present. The compound of Formula III is isolated and purified using techniques well known by those who practice the art of organic synthesis. For example, isolation of the compound of Formula III may be achieved by neutralizing the resin eluant with triethylamine, dissolving the residue in dichloromethane, and then washing with water, cold 1M HCl and saturated sodium bicarbonate solution. Purification may be accomplished by Silica Gel chromatography using ethyl acetate-hexane as eluant.

The reaction process provided by this invention is useful for the preparation of 2-deoxypyranoses and 2-deoxypyranosides, which are important components of many biologically active natural compounds including compactin, olivimycin, mithramycin and daunomycin.

The specially activated sulfonic acid and the process of making such resin provided by this invention are useful for the catalysis of reactions such as the one-step synthesis of 2-deoxy sugars from the corresponding glycals.

EXAMPLES

In the following examples, analytical grade cation exchange resin AG® 50W X2 (100–200 mesh) was purchased from Bio-Rad Laboratories (Richmond, Calif.). All solvents were purified according to the standard procedure (Perrin, D. D.; Armarego, W. L. F.; Perrin, D. R. Purification of Laboratory Chemicals Second Edition, Pergamon Press, N.Y., 1980) herein incorporated by reference. 3,4,6-Tri-O-acetyl-D-galactal, 3,4-di-O-acetyl-L-fucal- and L-rhamnal, and D-lactal-hexacetate were prepared according to the published procedures (Roth, W.; Pigman, W. Methods in Carbohydrate Chemistry, Whistler, R. L.; Wolfrom, M. L. Eds.; Academic Press: N.Y., 1962; p 405; Iselin, B.; Reichstein, T.; Helv. 1944, 27, 1146–1149; Haworth, W. N.; Hirst, E. L.; Streight, H. R.; Thomas, H. A.; Webb, I. J. J. Chem. Soc. 1930, 2639) each herein incorporated by reference. All other reagents were purchased from Aldrich Chemical Co. Thin layer chromatography was performed on precoated plates of Silica Gel 60 $F_{254}$ (EM Science, Gibbstown, N.J.), and the spots were visualized with a spray containing 5% sulfuric acid in ethanol followed by heating. Column chromatography was performed on Silica Gel 60 (230–400 mesh, EM Science). $^1$H NMR spectra were recorded at 500 MHz (GE Omega-500) and the chemical shifts in CDCl$_3$ are expressed relative to tetramethylsilane.

EXAMPLE 1

2-Deoxy-3,4,6-tri-O-acetyl-D-lyxo-hexo-pyranose (2-deoxy-3,4,6-tri-O-acetyl-D-galactopyranose)

Analytical grade cation exchange resin (50.0 g, Bio-Rad, Ag 50W-X2, 100–200 mesh, 72–84% by weight moisture content) was washed with deionized water (5 × 60 ml) and then with reagent grade acetonitrile (10 × 70 ml). The resin was then dried under vacuum (0.1 mm Hg) for 16 h. The weight of the dry resin was 10.0 g. Next, a solution of 3,4,6-tri-O-acetyl-D-galactal (5.0 g) and lithium bromide hydrate (5.0 g) in acetonitrile (150 ml), activated resin (3.0 g) and water (6 ml) were combined and stirred at room temperature for 15 min. The solution was filtered and neutralized with triethylamine and evaporated to dryness. The residue was dissolved in dichloromethane and washed with water, ice cold 1M hydrochloric acid and saturated sodium bicarbonate solution. Evaporation of solvent left a syrup which was purified on a column of Silica Gel using ethyl acetate-hexane as eluant, and yielded the title compound (4.38 g). $[\alpha]_D^{20} = +85.8° \pm 2°$ (c 0.96, CHCl$_3$). $^1$H NMR ∂: 5.48 (d, H-4α), 5.35 (m, H-3α), 5.33 (d, H-1α), 5.24 (H-4β), 4.99 (m, H-3β), 4.90 (dd, H-1β), 4.40 (t, H-5α), 4.0–4.15 (m, H-6α, H-6β), 3.85 (t, H-5β). MS (calculated mass for $C_{12}H_{18}O_8 = 291.11$). Obs. m/e 273.15 (M-H$_2$O), 213.12, 153.09.

EXAMPLE 2

Methyl 2-deoxy-3,4,6-tri-O-acetyl-α-D-lyxo-hexopyranoside (Methyl 2-deoxy-3,4,6-tri-O-acetyl-O-acetyl-α-D-galactopyranoside)

A solution of 3,4,6-tri-O-acetyl-D-galactal (11.0 g) in acetonitrile (110 ml) containing anhydrous lithium bromide (12 g), methanol (25 ml), molecular sieves 3 Å (4 g) and the activated resin prepared as in Example 1 (17 g) was stirred at room temperature for 4 h. The product was isolated as described for Example 1 and purified on a column of Silica Gel using ethyl acetate-hexane as eluant and yielded the title compound (10.9 g, $\alpha:\beta=3:1$). $[\alpha]_D^{20}$ ($\alpha$ anomer) = $+143°\pm2°$ (c 1.05, CHCl$_3$). $^1$H NMR ($\alpha$ anomer) $\delta$: 5.30 (d, H-4), 5.25 (m, H-3), 4.88 (d, H-1), 4.05–4.15 (m, H-6a,b, H-5), 3.33 (s, -OCH$_3$), 2.05 (m, H-2eq), 1.85 (m, H-2ax). MS (calc. mass for C$_{13}$H$_{20}$O$_8$=304.12) Obs. m/e 303.15 (M-1), 273.15 (M- CH$_3$OH), 213.13, 153.10.

EXAMPLE 3

Allyl 2-deoxy-3,4,6-tri-O-acetyl-α-D-lyxo-hexopyranoside (Allyl 2-deoxy-3.4.6-tri-O-acetyl-α-D-galactopyranoside]

A solution of 3,4,6-tri-O-acetyl-D-galactal (5.0 g) in acetonitrile (50 ml) containing anhydrous lithium bromide (5.45 g), allyl alcohol (11.5 ml), molecular sieves 4 Å (4 g) and the activated resin prepared as in Example 1 (7.3 g) was stirred at room temperature for 30 min. The product was isolated as described for Example 1 and purified on a column of Silica Gel using ethyl acetate-hexane as eluant and yielded the title compound (4.0 g) and minor β-glycoside (0.5 g). $[\alpha]_D^{20}$ (α-anomer) = $+126°\pm2°$ (c 1.03, CHCl$_3$); $[\alpha]_D^{20}$ (β-anomer) = $-17.7°\pm2°$ (c 1.02, CHCl$_3$). $^1$H NMR α anomer δ: 5.88 (m, —CH=C), 5.33–5.16 (H-1, H-3, C=CH$_2$), 5.04 (dd, H-4), 4.15 (H-5), 4.13 & 3.95 (m, O-CH$_2$), 4.07 (dd, H-6a,b), 2.07 (m, H-2eq), 1.87 (m, H-2ax). MS (α-anomer) (calc. mass for C$_{15}$H$_{22}$O$_8$=330.14). Obs. m/e 329.04, 273.04, 213.04.

EXAMPLE 4

4-Pentenyl 2-deoxy-3,4,6-tri-O-acetyl-α-D-lyxo-hexopyranoside

A solution of 3,4,6-tri-O-acetyl-D-galactal (3.6 g) in acetonitrile (40 ml) anhydrous lithium bromide (4.7 g), 4-pentene-1-ol (4 ml), molecular sieves 4 Å (4 g) and the activated resin prepared as in Example 1 (5.1 g) was stirred at room temperature for 30 min. The product was isolated as described in Example 1 and purified on a column of Silica Gel using ethyl acetate-hexane (1:6) as eluant and yielded the title compound (2.92 g) and minor β-glycoside (0.32 g). $[\alpha]_D^{20}$ (α-anomer) = $+126°\pm2°$ (c 1.03, CHCl$_3$); $[\alpha]_D^{20}$ (β-anomer) = $-9.4°\pm2°$ (c 1.03, CHCl$_3$) $^1$H NMR δ (α anomer): 5.81 (m, —CH=C), 5.33 (d, H-1), 5.28 (m, H-3), 4.94–5.06 (m, H-4, C=CH$_2$), 4.16–4.06 (H-6a,b, H-5), 3.65 and 3.40 (m, O-CH$_2$-), 2.1 (m, H-2eq), 1.86 (m, H-2ax) MS (calc. mass for C$_{17}$H$_{26}$O$_8$=358.17). Obs. m/e 571.33, 357.21, 299.19, 273.05, 213.11.

EXAMPLE 5

2-Deoxy-3,4,6-tri-O-acetyl-D-arabino-hexo-pyranose (2-deoxy-3,4,6-tri-O-acetyl-D-glucopyranose)

To a solution of 3,4,6-tri-O-acetyl-D-glucal (25.0 g) and lithium bromide hydrate (25.0 g) in acetonitrile (750 ml), activated resin prepared as in Example 1 (25.0 g) and water (30 ml) were added and stirred at room temperature for 4 h. The product was isolated as described for Example 1. Crystallization from ethyl acetate-hexane gave the title compound as colorless crystals (17.8 g). $[\alpha]_D^{20}$ = $+71.2°\pm2°$ (c 1.06, CHCl$_3$). $^1$H NMR δ: 5.40 (broad s, H-1α), 5.35 (m, H-3α), 4.9–5.05 (H-4α,β, H-3β, H-1β), 4.18–4.28 (H-6a, H-5α), 4.10 (H-6bβ), 4.06 (H-6bα). 3.65 (m, H-5β), 2.38 (m, H-2eqb), 2.25 (H-2eqα), 1 79 (H-2axα), 1.67 (H-2axβ). MS m/e 273.11 (M-H$_2$O), 213.10, 153.07.

EXAMPLE 6

5-Methoxycarbonylpentyl 2-deoxy-3,4,6-tri-O-acetyl-α-D-arabino-hexo-pyranoside (5-methoxycarbonylpentyl 2-deoxy-3.4,6-tri-O-acetyl-α-D-glucopyranoside)

A solution of 3,4,6-tri-O-acetyl-D-glucal (5.0 g) in acetonitrile (60 ml) containing anhydrous lithium bromide (5.6 g), 5-methoxycarbonylpentan-1-ol (5 ml), molecular sieves 4 Å (4 g) and the activated resin prepared as in Example 1 (7.6 g) was stirred at room temperature for 5 h. The product was isolated as described for Example 1 and purified on a column of Silica Gel using ethyl acetate-hexane (1:6) as eluant and yielded the title compound (5.3 g). $[\alpha]_D^{20}$ = $+76.2°\pm2°$ (c 0.98, CHCl$_3$). $^1$H NMR δ: 5.28 (m, H-3), 4.94 (t, H-4), 4.90 (broad d, H-1), 4.27 (dd, H-6a), 4.02 (dd, H-6b), 3.92 (m, H-5), 3.65 )s, OCH$_3$), 3.62 and 3.32 (m O-CH$_2$), 2.31 (t, CH$_2$COO), 2.20 (m, H-2eq), 1.78 (m, H-2ax) MS (calc. mass=418.19), Obs. m/e 419.23 (M+1), 273.13, 213.14, 153.10.

EXAMPLE 7

1,2,3,4-Di-O-isopropylidene-6-O-(2-deoxy-3,4,6-tri-O-acetyl-a-D-arabino-hexopyranosyl)-D-galactopyranose To a solution of 1,2,3,4-di-O-isopropylidene-α-D-galactopyranose (3.8 g) in anhydrous acetonitrile (100 ml) containing anhydrous lithium bromide (4.0 g), activated resin prepared as in Example 1 (2.5 g), and 4 Å molecular sieves, a solution of 3,4,6-tri-O-acetyl-D-glucal (6.0 g) in acetonitrile (40 ml) was added and the solution was stirred under nitrogen for 8 days. The reaction mixture was worked up as described for Example 1 and the title compound was obtained (2.5 g) by purification on a column of Silica Gel using ethyl acetate-hexane (3:8) as eluant. $[\alpha]_D^{20}$ = $+24.3°\pm2°$ (c 0.97, CHCl$_3$). $^1$H NMR δ: 5.51 (d, H-1), 5.31 (m, H-3'α), 5.01 (t, H-4'), 5.01 (d, H-1'), 4.62 (dd, H-3), 4.35 (m, H-6'a, H-4), 4.26 (dd, H-6'b), 4.04 (m, H-2, H-5'), 3.96 (m, H-5), 3.75 (dd, H-6a), 3.66 (dd, H-6b), 2.28 (dd, H-2'eq), 2.01, 2.04, 2.01 (3×s, OCOCH$_3$), 1.83 (m, H-2'ax), 1.56, 1.44, 1.35 & 1.34 (4×s, CH$_3$ of isopropylidene group). MS (calc. mass=532). Obs. m/e 531.00, 516.97, 273.00, 213.00 (100%).

EXAMPLE 8

1-S-Ethyl 2-deoxy-3,4,6-tri-O-acetyl-a,b-D-arabinohexopyranoside

To a solution of the compound of Example 5 (1.0 g) in acetonitrile (30 ml), ethyl mercaptan (1.6 ml), activated resin prepared as in Example 1 (0.6 g) and lithium bromide hydrate (1.0 g) were added and the solution was stirred at room temperature for 18 h. The reaction mixture was worked up as described for Example 1 and the product was isolated by chromatography on a column of Silica Gel. The weight of α and β anomers were 0.34 and 0.17 g, respectively. $[\alpha]_D^{20}$(α-anomer) = $+183.2°\pm2°$ (c 1.0, CHCl$_3$). $[\alpha]_D^{20}$(b-anomer) = $-41.7°\pm2°$ (c 1.02, CHCl$_3$). MS (calc. mass=334). Obs. m/e 333.16, 273.17, 213.13.

EXAMPLE 9

2,6-Dideoxy-L-lyxo-hexopyranose (2-Deoxy-L fucose)

To a solution of 3,4-di-O-acetyl-L-fucal (5.0 g) and lithium bromide hydrate (5.0 g) in acetonitrile (150 ml), activated resin prepared as in Example 1 (3.0 g) and water (6 ml) were added and stirred at room temperature for 15 min. The product was isolated as described for Example 1. Purification by chromatography on a column of Silica Gel using ethyl acetate-hexane (3:8) as eluant gave the title compound (4.0 g). $\alpha:\beta=9:4$. $[\alpha]_D^{20}=-57.6°\pm2°$(c 1.03, CHCl$_3$). $^1$H NMR $\delta$: 5.45 (d, H-1$\alpha$), 5.35 (m H-3$\alpha$), 5.19 (H-4$\alpha$), 5.10 (d, H-4$\beta$), 4.98 (m, H-3$\beta$), 4.87 (dd, H-1$\beta$), 4.33 (H-5$\alpha$), 3.73 (m, H-5$\beta$), 2.04 & 1.86 (m, H-2). MS (calc. mass=232). Obs. m/e 231.13, 215.12, 155.09 (100%).

EXAMPLE 10

Methyl 2,6-dideoxy-3,4-di-O-acetyl-α-L-lyxohexopyranoside (Methyl 2-deoxy-3,4-di-O-acetyl-α-L-fucopyranoside)

To a solution of 3,4-di-O-acetyl-L-fucal (2.0 g) and anhydrous lithium bromide (2.2 g) in acetonitrile (20 ml), activated resin prepared as in Example 1 (2.5 g) and methanol (1 ml) were added and stirred at room temperature for 5 h. The product was isolated as described for Example 1. Purification by chromatography on a column of Silica Gel using ethyl acetate-hexane (3:7) as eluant gave the title compound (1.6 g). The weight of the $\beta$ anomer was 0.33 g. $[\alpha]_D^{20}$ ($\alpha$-anomer)$=-174.2°\pm2°$ (c 1.00, CHCl$_3$). Lit. (Korytnyk, W.; Sufrin, J. R.; Bernacki, R. J. Carbohydr. Res. 1982, 103, 170–175) $-166°$ (c 0.79, CHCl$_3$). $[\alpha]_D^{20}$ ($\beta$-anomer)$=-13.6°\pm2°$ (c 1.02, CHCl$_3$). $^1$H NMR $\delta$: 5.24 (m, H-3), 5.15 (d, H-4), 4.83 (dd, H-1), 4.03 (m, H-5), 3.31 (s, OCH$_3$), 2.01 (m, H-2eq), 1.82 (m, H-2ax), 2.13 & 1.95 (2×s, $\overline{CH_3COO}$). MS (calc. mass=246). Obs. m/e 245.18, 215.17, 155.13 (100%).

EXAMPLE 11

2,6-Dideoxy-3,4-di-O-acetyl-L-arabino-hexopyranose (2-deoxy-L-rhamnose)

To a solution of 3,4-di-O-acetyl-L-rhamnal (5.0 g) and lithium bromide hydrate (5.0 g) in acetonitrile (150 ml), activated resin prepared as in Example 1 (3.0 g) and water (6 ml) were added and stirred at room temperature for 15 min. The product was isolated as described for Example 1. Purification by chromatography on a column of Silica Gel using ethyl acetate-hexane 3:8) as eluant gave the title compound (3.75 g). $\alpha:\beta=2:1$. $[\alpha]_D^{20}=-96.8°\pm2°$ (c 0 96. CHCl$_3$). $^1$H NMR $\delta$: 5.36 (H-1$\alpha$), 5.33 (m, H-3$\alpha$), 4.98 (m, H-3$\beta$), 4.90 (dd, H-1$\beta$), 4.75 (t, H-4), 4.12 (m, H-5$\alpha$), 3.54 (m, H-5$\beta$), 2.39 and 2.26 (m, H-2eq), 1.77 and 1.66 (m, H-2ax), 1.23 and 1.17 (d, CH$_3$). MS (calc. mass=232). Obs. m/e 231.13, 215.12, 155.09 (100 %).

EXAMPLE 12

5-Methoxycarbonylpentyl 4-O-(2,3,4,6-tetra-O-acetyl-β-D-galactopyranosyl)-2-deoxy-3.6-di-O-acetyl-α-D-arabinohexopyranoside A solution of lactal hexaacetate (18.3 g) in acetonitrile (100 ml) containing anhydrous lithium bromide (9.8 g), 5-methoxycarbonylpentan-1-ol (10 ml), molecular sieves 4 Å (4 g) and the activated resin prepared as in Example 1 (10 g) was stirred at room temperature for 16 h. The reaction mixture was worked up as described for Example 1 and the crude syrup was dissolved in dichloromethane (100 ml) containing pyridine (25 ml) and acetic anhydride (25 ml). After 16 h, the reaction mixture was diluted with dichloromethane, washed with water, ice cold IM hydrochloric acid and saturated sodium bicarbonate solution. The product was purified by chromatography on a column of Silica Gel. The weight of the syrupy product was 13.6 g. $[\alpha]_D^{20}=+13.0°\pm2°$ (c 1.00, CHCl$_3$). $^1$H NMR $\delta$: 5.33 (dd, H-4'), 5.27 (dd, H-3), 5.11 (dd, H-2'), 4.94 (dd, H-3'), 4.82 (dd, H-1), 4.54 (d, H-1'), 4.33 (dd, H-6a), 4.13 (m, H-6'a, H-6'b), 4.04 (dd, H-6b), 3.85 (m, H-5, H-5'), 3.63 (s. COO$\overline{CH_3}$), 3.63 (dd, H-4) 3.57 and 3.30 (m, O$\overline{CH_2}$-), 2.20 ($\overline{m}$, H-2eq.), 2.04 (m, H-2ax). MS (calc. mass=704.26). Obs. m/e 729.22, 705.22, 501.12 (100 %).

The claimed invention is:

1. A one-step reaction process for the preparation of 2-deoxypyranoses and 2-deoxypyranosides comprising combining a compound of Formula I with a compound of Formula II, in the presence of a specially activated sulfonic acid resin and halide ions, to produce a compound of Formula III;

wherein:

O$^a$ and O are each independently oxygen;

R$^1$ and R$^2$ are independently alkyl, alkenyl, alkynyl, aralkyl, aryl, acyl, aroyl, or a protected monosaccharide, disaccharide or polysaccharide, provided that for Formula I, the carbon of R$^1$ or R$^2$ directly bonded to O$^a$ is saturated; and for Formula II, the carbon of R$^3$ bonded to X is saturated;

Y is (CH-OR$^1$)$_n$Z, wherein:

Z is H or CH$_3$;

n is 0 to 4: and

R$^1$ is defined as above; X is oxygen or sulfur; and R$^3$ is H, hydrocarbyl, substituted hydrocarbyl, heterocyclic group, substituted heterocyclic group, or a protected sugar.

2. The process as recited in claim 1 conducted in a reaction solvent comprising acetonitrile, tetrahydrofuran, acetone, chloroform or nitromethane.

3. The process as recited in claim 1 conducted in a reaction solvent comprising acetonitrile.

4. The process as recited in claim 1 wherein the halide ions comprise soluble alkali metal chloride ions, soluble alkali metal bromide ions, tetraalkylammonium chloride ions, or tetraalkylammonium bromide ions.

5. The process as recited in claim 1 wherein the halide ions comprise lithium bromide, sodium bromide, potassium bromide, tetraethylammonium bromide, n-tetrabutylammonium bromide, tetraethylammonium chloride, or n-tetrabutylammonium chloride.

6. The process as recited in claim 1 wherein the halide ion is provided by addition of lithium bromide.

7. The process as recited in claim 1 wherein the compound of Formula I comprises 3,4,6-tri-O-acetyl-D-glucal; 3,4,6-tri-O-acetyl-D-galactal; 3,4-di-O-acetyl-L-fucal; 3-4-di-O-acetyl-L-rhamnal; or D-lactal hexaacetate.

8. The process as recited in claim 1 wherein the compound of Formula II comprises water; methanol; ethanol; propanol; butanol; allyl alcohol; 4-penten-1-ol; 5-methoxycarbonylpentan-1-ol; or 1,2,3,4-di-O-isopropylidene-D-galactopyranose.

9. The process of claim 1 wherein the sulfonic acid resin is specially activated by an activation process comprising
 a) washing a commercial or noncommercial sulfonic acid resin with water,
 b) further washing, 10 to 15 times in a volume equal to or greater than that of the resin, the sulfonic acid resin with a water-miscible polar, aprotic solvent, and
 c) drying the resin at room temperature under vacuum to remove residual solvent.

* * * * *